United States Patent [19]
Thornton et al.

[11] Patent Number: 5,360,917
[45] Date of Patent: Nov. 1, 1994

[54] PROCESS FOR PRODUCING MACROLIDE COMPOUNDS

[75] Inventors: Robert Thornton, Ulverson; David T. Eastlick, Grange-Over-Sands; Kenneth Briggs, Ulverston, all of England

[73] Assignee: Glaxo Group Limited, London, England

[21] Appl. No.: 385,825

[22] Filed: Jul. 27, 1989

Related U.S. Application Data

[63] Continuation of Ser. No. 24,665, Mar. 11, 1987, abandoned.

[30] Foreign Application Priority Data

Mar. 12, 1986 [GB] United Kingdom ................. 8606116

[51] Int. Cl.⁵ ........................................... C07D 323/00
[52] U.S. Cl. .................................................... 549/264
[58] Field of Search ......................................... 549/264

[56] References Cited

U.S. PATENT DOCUMENTS

| | | | |
|---|---|---|---|
| 4,173,571 | 11/1979 | Chabala et al. | 549/264 |
| 4,225,593 | 9/1980 | Davies et al. | 514/64 |
| 4,310,519 | 1/1982 | Albers-Schonberg et al. | 549/264 |
| 4,436,664 | 3/1984 | Gokel | 540/467 |
| 4,687,844 | 8/1987 | Gokel et al. | 540/467 |

FOREIGN PATENT DOCUMENTS 215654  9/1985  European Pat. Off.

*Primary Examiner*—G. Warren Ivy
*Assistant Examiner*—A. A. Owens
*Attorney, Agent, or Firm*—Bacon & Thomas

[57] ABSTRACT

A process for recovering at least one Antibiotics S541 compound or chemical derivative thereof from solution in an organic solvent, which comprises the steps of contacting the said solution with alumina and adsorbing the compound(s) thereon, eluting the compound(s) and collecting the eluate containing the compounds(s).

This method is suitable for the large scale separation of individual S541 compounds or mixtures thereof.

3 Claims, No Drawings

PROCESS FOR PRODUCING MACROLIDE COMPOUNDS

This application is a continuation of application Ser. No. 024,665 filed Mar. 11, 1987 now abandoned.

This invention relates to an improved process for the recovery and/or purification of antibiotic compounds. More particularly it relates to an improved process for the recovery and/or purification of antibiotic compounds produced by fermentation of Streptomyces microorganisms and chemical derivatives thereof.

United Kingdom Patent Specification No. 2166436 and European Patent Specification No. 170006 describe a class of substances, which we have designated Antibiotics S541. These have antibiotic and, in particular, anti-endoparasitic, anti-ectoparasitic, anti-fungal, insecticidal, nematicidal and acaricidal activity and are of special interest for use in agriculture, horticulture, and animal and human health. Antibiotics S541 substances are also of value as intermediates in the preparation of other compounds with such uses. Antibiotics S541 substances may be obtained by fermentation of Streptomyces microorganisms, in particular by fermentation of Antibiotics S541 producing strains belonging to the species *Streptomyces thermoarchaensis* and *Streptomyces cyaneorgriseus noncyanogenus*.

A number of isolation and separation techniques for obtaining Antibiotics S541 substances from the fermentation broths of producing microorganisms are described in the aforementioned UK and European Patent Specification. Thus, in general, following the fermentation of the microorganism, the cells are harvested and material containing Antibiotics S541 substances extracted therefrom using, for example, solvent extraction. The extracted material is then purified using fractionation techniques such as chromatography, solvent extraction, fractional crystallisation and precipitation to obtain individual Antibiotics S541 compounds as desired.

The methods of recovery and/or purification referred to above however may be inconvenient to operate on an industrial scale because of their complexity and the relatively low throughput of the desired product(s). Thus, for example, the use of silica chromatography on a large scale may be impractical because the system is easily overloaded and the desired products are generally not separated to the required level.

We have now found that Antibiotics S541 compounds and chemical derivatives thereof may be efficiently recovered from organic solution on a large scale by adsorption onto alumina and subsequent elution. In this way the compounds can easily be separated from impurities present in the solution and the process thus offers a convenient method for use in the purification of the compounds. In addition, we have found that by careful choice of the eluant and careful pretreatment of the alumina it is possible to selectively elute Antibiotics S541 compounds from the alumina.

Thus, in one aspect of the invention we provide a process for recovering an Antibiotics S541 compound or a chemical derivative thereof from an organic solution, which comprises the steps of contacting the said solution with alumina suitable for adsorbing the compound, eluting the compound and collecting the eluate containing the compound.

It will be appreciated that the process according to the invention may be applied to a solution containing a mixture of Antibiotics S541 compounds and the invention is thus to be understood to extend to a process for recovering two or more Antibiotics S541 compounds from an organic solution thereof, said process comprising the steps of contacting the said solution with alumina suitable for adsorbing the Antibiotics S541 compounds, eluting the Antibiotics S541 compounds if desired in a selective manner and collecting the eluate(s) containing the Antibiotics S541 compound(s).

The Antibiotics S541 compounds which may be recovered according to the process of the invention will in general be any Antibiotics S541 compounds or derivatives thereof produced by an Antibiotics S541 producing microorganism belonging to the genus Streptomyces especially an Antibiotics S541 producing strain of the species *Streptomyces thermoarchanensis* or *Streptomyces cyaneorgrisus noncyanogenus*. Particular strains include *Streptomyces thermoarchaensis* NCIB 12015, NCIB 12111, NCIB 12112, NCIB 12113 and NCIB 12114 and *Streptomyces cyaneorgriseus noncyanogenus* NNRL 15773 and mutants of these strains. Microorganisms capable of producing Antibiotics S541 compounds may readily be identified using a convenient small scale test employing the nematode *Caenorhabditis elegans*, for example by adding a test sample [obtained from fermentation of the microorganism as described herein] to a suspension of the nematode and examining the consequent effect on nematode viability.

In particular, the compounds which may be recovered may have a partial formula (I)

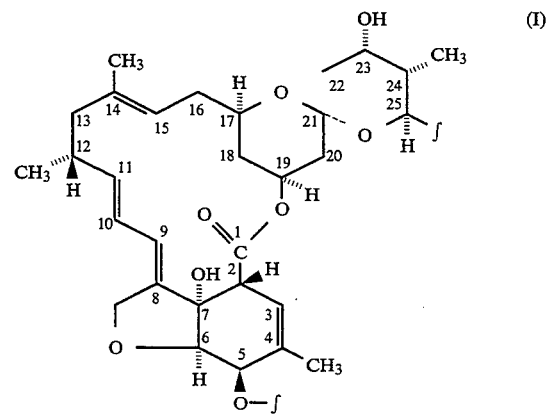

and especially a partial formula (II)

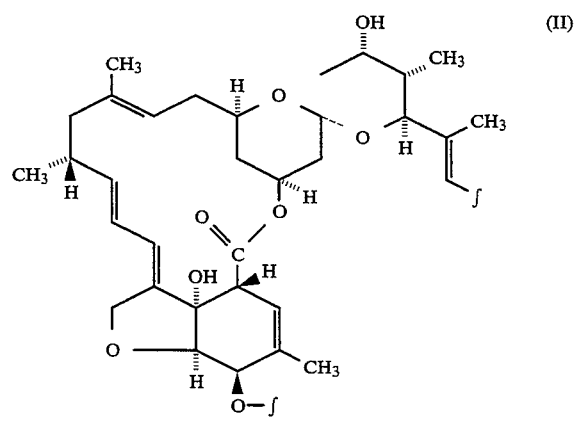

and are preferably compounds of formula (III)

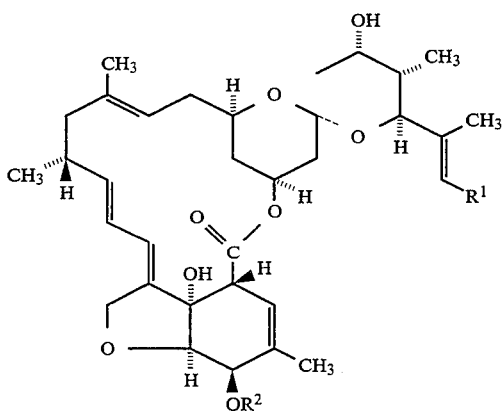

(III)

[where $R^1$ is a methyl, ethyl or isopropyl group and $OR^2$ is a hydroxy or methoxy group]

A particularly preferred Antibiotics S541 compound which may be recovered is a compound of formula (III) wherein $R^1$ is an isopropyl group and $OR^2$ is a hydroxy group.

The process according to the present invention is particularly useful for the purification of antibiotic compounds which are chemical derivatives of Antibiotics S541 substances. Chemical derivatives which can be purified may be any chemical derivatives of an Antibiotics S541 substance. Thus, for example, the chemical derivatives may be derivatives of compounds of formula (III) such as compounds described in UK Patent Specification No. 23176182. Particular chemical derivatives which may be purified include compounds of formula (III) in which $R^1$ is a methyl, ethyl, or, more especially, an isopropyl group and $OR^2$ is a protected hydroxyl group (e.g. acetoxy or 2,2,2-trichloroethoxycarbonyloxy).

In general the organic solution from which the Antibiotics S541 compound or a chemical derivative thereof is to be recovered using the process of the invention (hereinafter referred to as the input solution) will desirably be a solution of the compound in a solvent (hereinafter referred to as the input solvent) such as a hydrocarbon e.g. petroleum ether, hexane or an aromatic hydrocarbon such as toluene, a chlorinated hydrocarbon e.g. carbon tetrachloride or dichloromethane or an ester e.g. ethyl acetate or butyl acetate, or if desired, mixtures thereof, If desired a small volume of a more polar solvent such as a ketone, e.g. acetone, a nitrile, e.g. acetonitrile, an ester, e.g. ethyl acetate, or an ether, e.g. dioxan, may also be present, generally in a proportion of less than 10% of the total volume of the input solution to effect better separation. The input solvent is preferably petroleum ether optionally containing up to 10% acetone.

The input solution may be obtained following conventional extraction techniques for the Antibiotics S541 compound(s). Thus, the input solution may be obtained by extraction of suitable material containing the Antibiotics S541 compound(s) by means of conventional techniques using the input solvent. The suitable material to be extracted may conveniently be mycelia previously obtained by fermentation of an Antibiotics S541 producing strain of Streptomyces or an extract thereof in an organic solvent which is immiscible with the input solvent but which is miscible with water. Such an organic solvent may be an alcohol, e.g. methanol or propan-2-ol, a diol, e.g. propan-1,2-ol or butan-1,3-ol, an amide, e.g. formamide or dimethylformamide, a nitrile, e.g. acetonitrile, a ketone, e.g. acetone or an ether, e.g. dioxan. Alternatively the input solution may be obtained by dissolving the input solvent Antibiotics S541 compounds which have already been partially purified from mycelis and obtained as solids (e.g. using the general separation/purification techniques described herein), or a partially purified chemical derivative of an Antibiotics S541 compound (e.g. prepared according to the conventional techniques described in UK Patent Specification No. 2176182).

Mycelia containing Antibiotics S541 compounds may be obtained by fermentation of an Antibiotics S541 producing Streptomyces organism by conventional means i.e. by culturing the Streptomyces organism in the presence of assimilable sources of carbon, nitrogen and mineral salts according to the methods described in UK Patent Specification No. 2166436 and European Patent Specification No. 170006.

The alumina which may be used in the process of the invention may typically have a surface area of from 5 to 500 m²/gm. The alumina will in general be chromatographic grade alumina and may be for example Laporte alumina (UG) or Camag 5016 alumina.

The input solution may be brought into contact with the alumina in any desired way, (preferably after conditioning the alumina with one or more suitable solvents, for example as described below for the regeneration of the alumina) most suitably by passing it through a column or bed or the alumina. If desired some alumina may be slurried with the input solution when a column system is used; the slurrying is conveniently effected prior to filling the column.

It will be appreciated that it is possible to exceed the capacity of the alumina for adsorbing the antibiotic compound(s). To prevent unnecessary loss of material it is desirable to either determine the capacity of the alumina for a particular input solution by appropriate small scale tests beforehand, or, when a column system is used, to monitor the eluate for the presence of the compound (e.g. using the techniques described below) as the input solution is loaded. The capacity of any alumina for a particular compound will vary depending on e.g. the nature of the input solution and the number of impurities present which are also capable of being adsorbed. In general, we have found that alumina may adsorb in a working range of 10–100 g of the antibiotic compound(s) per liter of alumina, preferably in the range of 15–45 g/L.

When the compound(s) have been adsorbed on the alumina, the alumina may be washed (e.g. with a hydrocarbon solvent, preferably the input solvent or a mixture thereof with a polar solvent e.g. acetone) prior to elution, to remove impurities not bound to the alumina. It may be convenient to wash the alumina successively with a mixture of solvents in which the proportion of polar solvent is increased in a stepwise manner. It is thus preferred to wash the column following the use of petroleum ether as input solvent with mixtures of petroleum ether and acetone where the acetone content is increased stepwise up to 25%, but preferably at lower levels e.g. up to 10%.

The antibiotic compound(s) may be eluted from the alumina, for example using an organic solvent that is more polar than the input solvent. Examples of such solvents include alcohols such as methanol or propan-2-ol, ketones such as acetone, nitriles such as acetonitrile or esters such as ethyl acetate or mixtures thereof or mixtures with less polar solvents including the input solvent. Optionally water comprising up to 5% of the total volume of the eluant may be admixed with the solvent or mixtures of solvents. Preferably the eluant is acetone containing up to 5% water.

The adsorption and elution of an antibiotic compound on the alumina may be conveniently effected at a temperature from −10° to 50° C., preferably 15° to 25° C. Rates of loading the elution of the compound on the alumina may in general lie in the range 0.25 to 10, preferably in the range 0.5 to 2 bed volumes per hour.

The initial eluate forerun obtained during elution of the alumina may be discarded until the elution of the antibiotic compound(s) commences. At that time, the fractions containing the antibiotic compound(s) are collected until the desired compound has been substantially eluted. The presence of a compound in the eluate may be determined by monitoring the eluate by high performance liquid chromatography, uv spectroscopy at 238 nm, optical activity or other physical parameters.

When a column system is used, the alumina may be regenerated after use and then re-used. Suitable regeneration means include contacting the alumina with a volume of water and water miscible organic solvent, e.g. 50% acetone-water, containing a base, e.g. sodium hydroxide, sufficient to elute adsorbed yellow pigments from the alumina. The column is then washed with water and treated with an acid e.g. acetic acid to neutralise excess alkalinity. The alumina may be at an acid, neutral or basic pH in the range 3–11 when used. The choice of pH will, of course, depend on the antibiotic compound(s) to be loaded and eluted on the column. In general, the fermented Antibiotics S541 factors are preferably loaded onto alumina adjusted to a basic pH whereas chemical derivatives thereof, such as the 5-acetate of Factor A, are preferably loaded onto alumina adjusted to an acidic pH.

When a column system is used, we have found that separation of the Antibiotics S541 compounds during elution is improved if the column is pretreated before loading the Antibiotics S541 compounds. Suitable pretreatment means include contacting the alumina with a suitable water miscible solvent e.g. acetone or preferably methanol (the first wash solvent), followed by washing with the input solvent to reduce the amount of the first wash solvent in the input solvent percolate to an acceptably low level, e.g. less than about 5%.

General, pretreatment of the alumina is carried out after the regeneration procedures.

Rates of washing and the temperature at which the pretreatment and/or regeneration is performed may be, for example, as described previously for the adsorption and elution of the compounds.

It will be appreciated that when the input solution contains more than one Antibiotics S541 compound and all such compounds have been adsorbed by the alumina, then the elution conditions may be chosen to effect a degree of chromatographic separation of the Antibiotics S541 compounds, e.g. by using eluants of increasing polarity in a stepwise elution.

In a further aspect of the invention we provide a process for the separation of Antibiotics S541 compounds in admixture in an organic solution which comprises the steps of contacting the said solution with alumina suitable for absorbing the Antibiotics S541 compounds, eluting the compounds in a stepwise manner using eluants of increasing polarity and collecting the eluates containing the desired compounds. The use of alumina pretreated in the manner described above is particularly suitable for the separation and purification of Antibiotics S541 compounds from a mixture thereof.

We have found in particular that it is possible to obtain a satisfactory degree of separation of compounds of formula (III) in which $R^2$ is a hydrogen atom and compounds of formula (III) in which $R^2$ is a methyl group using a selective elution technique. Thus in a further aspect of the invention we provide a process for the separation of a compound of formula (III) IN which $R^2$ is a hydrogen atom and a compound of formula (III) in which $R^2$ is a methyl group in admixture in an organic solution which comprises the steps of contacting the said solution with alumina suitable for adsorbing the compounds of formula (III), especially alumina pretreated in the manner described above, eluting the compound of formula (III) in which $R^2$ is a methyl group and collecting the eluate containing said compound, and subsequently eluting the compound of formula (III) in which $R^2$ is a hydrogen atom and collecting the eluate containing said compound.

Thus, the Antibiotics S541 compounds may be absorbed on the alumina using an input solution such as is described above. Selective elution may then be achieved by first washing the alumina with a solvent that is sufficiently more polar than the input solvent to elute the compound of formula (III) in which $R^2$ is a methyl group but to leave the compound of formula (III) in which $R^2$ is a hydrogen atom adsorbed on the alumina. The eluting solvent may conveniently be, for example, the input solvent to which a more polar solvent has been added. Suitable eluting solvents are as previously described in the general discussion of this input solvent. A particularly convenient eluting system is petroleum ether containing a small volume of acetone (e.g. up to 10%). Once the compound of formula (III) in which $R^2$ is a methyl group has eluted the eluting solvent is changed to a more polar solvent, which is preferably acetone containing up to 5% water, to elute the compound of formula (III) in which $R^2$ is a hydrogen atom. A particularly convenient system for eluting the compound of formula (III) in which $R^{22}$ is a hydrogen atom is acetone/water e.g. in a ratio of 99 parts acetone to 1 part water. This procedure is particularly useful for the preparation of a compound of formula (III) in which $R^1$ is isopropyl and $R^2$ is a hydrogen atom.

The compounds obtained according to the process of the invention may be used directly, preferably after removal of the elution solvent, in one of the applications described above. Alternatively, the compounds may be subjected to further conventional fractionation techniques such as chromatography, solvent extraction, fractional crystallisation or precipitation as desired, before use or before further chemical derivatisation.

The following Examples illustrate the invention.

In the following Examples, the compounds are named by reference to the known "Factors", Factors A and B. Factor A is the compound of formula (III) in which $R^1$ is an isopropyl group and $R^2$ is a hydrogen atom and Factor B is the compound of formula (III) in which $R^1$ is a methyl group and $R^2$ is a methyl group.

The following abbreviations are used: PF—petroleum ether (b.p. 60°–80° C.); L—liter.

Regeneration of the alumina used in the Examples was achieved by the following method adjusted pro rata for the volume of alumina used:

The alumina column (1 bed volume, 1 BV) was treated with 50% acetone-water (5 BV) containing 1% w/v sodium hydroxide, followed by water (4BV). The alumina slurry was treated with acetic acid to a suitable pH and finally washed with water (2 BV). All regenerant streams were applied at 2BV per hour.

Occasionally, extra alkaline acetone-water may be required.

Preparation 1

Bulked harvest broth (520 L) obtained using the method of Example 7 in UK Patent Specification 2166436 was mixed with Dicalite 478 (5.2 Kg), and was filtered on a rotary vacuum filter with a precoat bed of Rettenmaier cellulose BEOO. The cell paste with admixed filter aid was stirred into enough methanol to give a final volume of 80 L. After 40 min the suspension was filtered through at will cloth with a 12 mm bed of Dicalite 478. The residue from the filtration was reextracted with methanol in the same way, and the methanol filtrates were combined (80 L). The methanol filtrates were mixed with water (20 L) re-extracted with PE and the PE extract concentrated to a final volume of 8.2 L.

Example 1

A column (150 ml) of Camag alumina (A-5016) was prepared in water after regeneration and treatment with acetic acid to pH 9. The column was treated with methanol (150 ml), followed by PE (450 ml), both liquids being applied at 300 ml/hour.

A crude solution of Factors A and B in PE [300 ml—containing Factor A (3.13 g) and Factor B (1.21 g)], obtained as in Preparation 1 was loaded downflow followed by PE (150 ml) at a rate of 300 ml/hour. Thereafter a wash of 10% v/v acetone-petrol (900 ml) was applied at 300 ml/hour. Only Factor B and trace (<0.5%) Factor A were found in the loading and wash percolates. Factor B was recovered from the PE percolates by concentration and filtering the resultant precipitated solid.

The column was then eluted with 99% acetone—1% water, collecting a forerun of 75 ml which contained 1% Factor A. A rich cut eluate (575 ml) was obtained, then concentrated to 72 ml and cooled.

About 25 ml of a 3:1 mixture of water (containing 0.1% v/v sulphuric acid) and acetone were cooled to 0°-5° C. and stirred. To the stirred mixture was added over 90 minutes simultaneously, the cold concentrated rich cut eluate (72 ml) and cold water containing 0.1% v/v sulphuric acid (216 ml). The slurry was stirred for 10 min, filtered and the solid washed with 24 ml of cold 25% acetone-water followed by 3×24 ml aliquots of water.

The product was dried to give a solid containing 2.70 g Factor A (86.3% yield from input solution). The solid contained no Factor B.

Example 2

A column (2000 ml) of Camag alumina (A-5016) was prepared in water after regeneration and treatment with acetic acid to pH 9. The column was treated with methanol (2000 ml), followed by PE (6000 ml), both liquids being applied at 4000 ml/hour.

A crude solution of Factors A and B in PE—acetone (19:1) [4000 ml containing Factor A (52.70 g), and Factor B (13.26 g] obtained as in Preparation 1 was loaded downflow followed by PE (2000 ml). Thereafter a wash of 12000 ml of 10% acetone-PE was applied at 4000 ml per hour. Only Factor B (11.65 g) was detected in the loading and wash percolates. Factor B was recovered from the PE percolates by concentration and filtering the precipitated solid.

The column was eluted with b 99% acetone—1% water, collecting a forerun of 970 ml which contained only a trace (0.2%) of Factor A. The rich cut eluate (8010 ml) was concentrated to 1300 ml.

The concentrated rich cut eluate (1300 ml) was added over 1 hour to cold water containing 0.1% v/v sulphuric acid (7800 ml) with good stirring. The solid was washed with 3×400 ml water and dried. The solid contained 50.0 g Factor A (95% yield from input solution).

Example 3

A column (100 ml) of Camag alumina (A-5016) was prepared in water after regeneration and treatment with acetic acid to pH 9. The column was washed with acetone (300 ml) followed by PE (300 ml), both streams being applied at 200 ml/hour.

A crude solution of Factors A and B in PE [186 ml—containing Factor A (2.52 g) and Factor B (1.31 g)] obtained as in Preparation 1 was loaded downflow, followed by PE (100 ml). Both liquids were applied at 200 ml/hour. Thereafter a wash of 10% acetone-PE (600 ml) was applied. No Factors were found in the loading percolate, but the wash percolate contained only Factor B (1.18 g). Factor B was recovered from the percolates by concentration and filtering the precipitated solid.

The column was eluted with neat acetone, discarding a forerun (40 ml) which contained only a trace of Factor B. The rich cut eluate (341 ml) was concentrated (40 ml) and added to rapidly stirred water containing 0.1% v/v sulphuric acid (240 ml) at 0°-5°.

The solid was filtered, washed with 3×20 ml of cold water and dried to a solid, which contained 1.87 g Factor A (74% yield from input solution).

Example 4

A column (1000 ml) of Camag alumina (A 5016) was prepared in water after regeneration and treatment with acetic acid to pH 9. The column was conditioned with methanol (1000 ml) followed by PE (3000 ml), both being applied downflow at 2000 ml/hr.

A crude solution of Factors A and B in PE ]1910 ml—containing Factor A (20.40 g) and Factor B (7.86 g)], obtained as in Preparation 1 was loaded downflow followed by PE (1000 ml). Thereafter a wash of 6000 ml of 10% acetone-petrol was applied downflow at 2000 ml/hour. The loading and wash percolates contained Factor B (6.80 g) and Factor A (0.4 g). Factor B was recovered from the PE percolates by concentration and filtering the precipitated solid.

The column was eluted using 99% acetone 1% water, discarding a forerun (450 ml) which contained Factor A (0.1 g). The rich cut eluate (4050 ml) was concentrated to 95 ml and cooled.

A mixture of 3:1 water (containing 0.1% v/v sulphuric acid) and acetone (total 25 ml) was stirred at 0°-5° C. To the stirred mixture was added over 90 min simultaneously, the cold concentrated rich cut eluate (95 ml) and cold water containing 0.1% sulphuric acid (285 ml). The slurry was stirred for 10 min, filtered, and the solid washed with 32 ml of cold 25% acetone water followed by 3×25 ml of cold water.

The product was dried to give a solid containing 4.52 g Factor A (88.6% yield from input solution). The solid contained no Factor B.

Example 5

A column (150 ml) of Camag alumina was prepared in water after regeneration and treatment with acetic acid to pH 9. The column was treated with methanol (150 ml) at 150 ml/hour followed by PE (470 ml) at 300 ml/hour.

A crude solution of Factors A and B in PE [154 ml—containing Factor A (3.38 g) and Factor B (1.80 g) obtained as in Preparation 1 and added acetone (6 ml)] was loaded downflow to the column at 300 ml/hour. Thereafter the column was treated at 300 ml/hour with successive 150 ml aliquots of 2%, 4%, 6%, 8% and 10% acetone-PE (total 900 ml). Only Factor B and a trace of Factor A was found in the washes. Factor B was recovered from the PE percolates by concentration and filtration of the resultant slurry.

The column was eluted with 99% acetone—1% water collecting a forerun of 75 ml which contained only a trace of Factor A. A rich cut eluate (550 ml) was collected, concentrated to 75 ml and chilled to 5°.

The eluate was added to water containing 0.1% v/v sulphuric acid (420 ml) at 5° with good stirring. The slurry was stirred for 10 minutes, filtered and the solid washed with 3×25 ml aliquots of water.

The product was dried to give a solid containing 3.55 g Factor A. The solid contained no Factor B.

Example 6

A column (100 ml) of Camag alumina (A-5016) was prepared in water after regeneration and treatment with acetic acid to pH 9. The column was treated with methanol (100 ml) at 200 ml/hour followed by PE (300 ml) at 100 ml/hour.

A crude solution of Factors A and B in PE (55 ml) containing Factor A (2.79 g) and Factor B (0.49 g) obtained as in Preparation 1 and added acetone (1.1 ml) was loaded downflow at 100 ml/hour. The column was washed successively with 3% acetone—97% PE (200 ml), 5% acetone —95% PE (200 ml), 25% acetone—75% PE (600 ml), all applied at 100 ml/hour. Factor B was retained in the loading percolate and 3% acetone—97% PE percolates free of Factor A. The remaining wash percolate contained other impurities and Factor A (0.654 g).

The column was eluted with 99.5% acetone—0.5% water at 100 ml/hour. The rich cut eluate was bulked, concentrated to 34 ml and cooled to 5° C. The solution (32 ml) was precipitated by adding to stirred water (200 ml) at 5° containing 0.1% v/v sulphuric acid over 60 minutes. The solid was filtered, washed well with water and dried. The purified dried solid contained 1.67 g Factor A (60% from the input solution) and no Factor B.

Example 7

A column (1 L) of Camag alumina (A-5016) was prepared in water after regeneration and treatment with acetic acid to pH 5.6. The column was treated with acetone (1 L) followed by PE (3 L), both liquids applied at 1 L/hour.

A crude solid (prepared according to the method of Example 7 in UK Patent Specification 2176182) containing 5-acetyl Factor A (12.50 g) and other impurities was dissolved in 3% acetone-PE (500 ml) and loaded downflow to the column at 1 L/hour. The column was washed with 8% acetone—92% PE (4 L) at 1 L/hour. The column was eluted with 15% acetone—85% PE at 1 L/hour. The eluate was monitored by HPLC and selected fractions bulked (2 L).

The bulked eluate was concentrated to 160 ml (acetone was removed by adding hexane during the evaporation) and extracted with b 4 aliquots (50 ml) of propan-1,2-diol. The diol solution was degassed in vacuo and precipitated into 1200 ml of cold (5°), well stirred water containing 0.1% v/v sulphuric acid. The slurry was stirred for 10 minutes, filtered and washed with cold water before drying. The yield of purified 5-acetyl Factor A was 48.4% and the impurity profile was reduced to 55% that of the input solution.

Example 8

A column (20 ml) of Camag alumina (A-5016) was prepared in water and treated with acetone (20 ml) followed by hexane (100 ml) at 40 ml/hour.

A crude solid containing Factor A (0.46 g) and other impurities was dissolved in hexane (10 ml) and loaded downflow to the column at 40–60 ml/hour. The column was eluted with 1,4-dioxan-hexane (20:80) at 40–60 ml/hour. The eluate was monitored by thin layer chromatography and high performance liquid chromatography and selected 10 ml fractions were bulked (82 ml).

The bulk eluate contained 85% of the input and the impurity profile was reduced to 71% of the input impurities.

Example 9

A column (20 ml) of Camag alumina (A-5016) was prepared in water and treated with acetone (20 ml) followed by hexane (100 ml) at 40 ml/;hour.

A crude solid containing Factor A (0.46 g) and other impurities was dissolved in hexane (10 ml) and loaded downflow to the column at 40–60 ml/hour. The column was eluted with ethyl acetate-chloroform (30:70) at 40–60 ml/hour. The eluate was monitored by thin layer chromatography ad high performance liquid chromatography and selected 10 fractions were bulked (30 ml).

The bulk eluate contained 43% of the input and impurity profile was reduced to 35% of the input impurities.

Example 10

A column (1 L) of Camag alumina (A-5016) was prepared in water, after regeneration and treatment with acetic acid to pH 5.0. The column was treated with acetone (1 L) followed by PE (3 L), both liquids were applied at 1 L/hour.

A crude solid (prepared according to Example 85 in UK Patent Specification 2176182) containing Factor A, 5-(2,2,2-trichloroethylcarbonate) (9.9 g) and other impurities was dissolved in 6% v/v acetone —PE (1100 ml) and loaded downflow to the column at 1 L/hour. The column was eluted with 15% v/v acetone—PE at 1 L/hour. The eluate was monitored by high performance liquid chromatography and selected fractions bulked (2 L) to give an upgraded recovery of 53% of the The bulked eluate was concentrated to 210 ml and extracted with 4 aliquots (70 ml) of propan-1,2-diol. The diol solution was degassed in vacuo, acetone (300 ml) was added and the mixture precipitated by simultaneous addition, with 0.1% v/v sulphuric acid (1500 ml), to a small volume of cold (5° C.) stirred dilute acid. The slurry was stirred for a further 10 minutes, filtered and washed with cold water before drying. The purified solid contained 2.3 g of Factor A5-(2,2,2-trichloroethylcarbonate) and had an impurity profile reduced to 54% of the input solution.

We claim:

1. In a process for recovering at least one Antibiotics S541 compound or chemical derivative thereof from solution in an organic solvent, wherein the improvement comprises the use of an organic solvent which is petroleum ether or a mixture thereof with up to 10% acetone, followed by contacting the said solution with alumina and absorbing the compound(s) thereon, eluting the compound(s) with an elution solvent which is an alcohol, ketone, nitrile or ester solvent or a mixture thereof with a less polar solvent and collecting the eluate containing the compounds.

2. In a process for recovering at least one Antibiotics S541 compound or chemical derivative thereof from solution in an organic solvent, wherein the improvement comprises the use of an organic solvent which is a hydrocarbon, chlorinated hydrocarbon or ester solvent, or a mixture of two or more of these solvents or a mixture with up to 10% of a more polar solvent, followed by contacting the said solution with alumina and absorbing the compound(s) thereon, eluting the compound(s) with an elution solvent which is acetone or a mixture thereof with up to 5% water and collecting the eluate containing the compounds.

3. In a process for recovering at least one Antibiotics S541 compound or chemical derivative thereof from solution in an organic solvent, wherein the improvement comprises the use of an organic solvent which is a hydrocarbon, chlorinated hydrocarbon or ester solvent, or a mixture of two or more of these solvents or a mixture with up to 10% of a more polar solvent, followed by passing the solution through a column of alumina and absorbing the compound(s) on the alumina, eluting the compound(s) with an elution solvent which is an alcohol, ketone, nitrile or ester solvent or a mixture thereof with a less polar solvent and collecting the eluate containing the compounds; said alumina being pretreated by contact with acetone or methanol.

* * * * *